United States Patent [19]
Mondadori

[11] Patent Number: 6,022,877
[45] Date of Patent: *Feb. 8, 2000

[54] USE OF (+)-α-(2,3-DIMETHOXYPHENYL-1-[2-(4-FLUOROPHENYL)ETHYL]-4-PIPERIDINEMETHANOL IN TREATING DEPRESSIVE DISORDERS AND BIPOLAR DISORDERS

[75] Inventor: Cesare Mondadori, Basking Ridge, N.J.

[73] Assignee: Hoechst Marion Roussel, Inc., Bridgewater, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/026,323

[22] Filed: Feb. 19, 1998

Related U.S. Application Data

[63] Continuation of application No. 08/823,658, Mar. 17, 1997, abandoned.

[30] Foreign Application Priority Data

Mar. 21, 1996 [EP] European Pat. Off. ............... 96400591

[51] Int. Cl.[7] .................................................. A61K 31/445
[52] U.S. Cl. ............................................................. 514/317
[58] Field of Search ............................................... 514/317

[56] References Cited

U.S. PATENT DOCUMENTS

| | | |
|---|---|---|
| 4,762,842 | 8/1988 | Cohen et al. . |
| 4,783,471 | 11/1988 | Carr et al. . |
| 4,877,798 | 10/1989 | Sorensen . |
| 4,902,691 | 2/1990 | Cohen et al. .............................. 514/288 |
| 4,908,369 | 3/1990 | Schechter et al. . |
| 4,912,117 | 3/1990 | Carr et al. . |
| 5,021,428 | 6/1991 | Carr et al. . |
| 5,064,838 | 11/1991 | Carr et al. . |
| 5,106,855 | 4/1992 | McLees . |
| 5,134,149 | 7/1992 | Carr et al. . |
| 5,169,096 | 12/1992 | Carr et al. . |
| 5,561,144 | 10/1996 | Carr et al. . |
| 5,618,824 | 4/1997 | Schmidt et al. . |
| 5,643,784 | 7/1997 | Bogeso et al. ......................... 514/228.8 |
| 5,700,812 | 12/1997 | Carr et al. . |
| 5,700,813 | 12/1997 | Carr et al. . |
| 5,721,249 | 2/1998 | Carr et al. . |

FOREIGN PATENT DOCUMENTS

| | | |
|---|---|---|
| 0319962 | 12/1988 | European Pat. Off. . |
| 0337136 | 3/1989 | European Pat. Off. . |
| 9118602 | 12/1991 | WIPO . |
| 9723220 | 7/1997 | WIPO . |

OTHER PUBLICATIONS

Kehne, John H. et al., The Jrnl of Pharmacology and Experimental Therapeutics, vol. 277, No. 2, pp 968–981, 1996.
Adis LMS Drug Alerts Abstract of Kennedy et al., Int. Clin. Psychopharmacol. 6 (Suppl. 1):54–72, Jul. 1991.
Anxiolytic Serotonin Antagonist: Drugs of the Future, vol. 14, No. 5 (pp. 489–490) (1989).
Psychopharmacology, vol. 96 (pp. 395–399) (1988).
Acta Psychiatr Scand, vol. 83 (pp. 244–248) (1991).
Drug Development Research, vol. 8 (pp. 205–211) (1986).
Sleep, vol. 16, No. 7 (pp. 647–654) (1993).
Journal of Clinical Psychopharmacology, vol. 13, No. 6 (pp. 409–414) (1993).
A. Sluzewska, et al., Behavioral Pharmacol. 5, Suppl. 1, p 86 (1994).
Willner, Pharmac. Ther. vol. 45, pp 425–455 (1990).
Willner, et al., Psychopharmacology 93, pp 358–364 (1987).
J.–L. Moreau et al., Behavioural Pharmacology, 5, pp 344–350 (1994).
Willner, TIPS. vol. 56, No. 25, pp 131–136 (1991).
C.J. Schmidt, et al., Life Sciences, vol. 56, No. 25, pp 2209–2222 (1995).
S.Kasper et al., Human Psychopharmacology, vol. 9, pp 1–12 (1994).
C.J. Schmidt et al., EP Journal of Pharmacology, vol. 273, No. 1/2, pp 273–279 (1995).
J.A. Den Boer et al., Human Psychopharmacology, vol. 10, pp S173–S183, (1995).
C.J. Schmidt et al., Life Sciences, vol. 56, No. 25 (1995).
G.J. Marek et al., European Journal of Pharmacology, vol. 259, No. 1, pp 137–141 (1994).

*Primary Examiner*—Raymond Henley, III
*Attorney, Agent, or Firm*—Carolyn D. Moon

[57] ABSTRACT

The present invention is directed to the use of (+)-α-(2,3-dimethoxyphenyl)-1-[2-(4-fluorophenyl)ethyl]-4-piperidinemethanol in treating Depressive Disorders and Bipolar Disorders.

1 Claim, No Drawings

USE OF (+)-α-(2,3-DIMETHOXYPHENYL-1-[2-(4-FLUOROPHENYL)ETHYL]-4-PIPERIDINEMETHANOL IN TREATING DEPRESSIVE DISORDERS AND BIPOLAR DISORDERS

This is a continuation of patent Ser. No. 08/823,658 filed Mar. 17, 1997, now abandoned.

The present invention is directed to the use of compound (+)-α-(2,3-dimethoxyphenyl)-1-[2-(4-fluorophenyl)ethyl]-4-piperidinemethanol or its pharmaceutically acceptable acid addition salts in a method of treating Depressive Disorders and Bipolar Disorders in patients in need of such therapy.

BACKGROUND OF THE INVENTION

The compound (+)-isomer of α-(2,3-dimethoxyphenyl)-1-[2-(4-fluorophenyl)ethyl]-4-piperidinemethanol is generically described by U.S. Pat. No. 5,169,096 and specifically described in U.S. Pat. No. 5,134,149, both of which are hereby incorporated by reference. This compound is described therein as a $5HT_{2A}$ receptor antagonist. It has since been discovered that this compound is useful in the treatment of Depressive Disorders and Bipolar Disorders.

The compound of the present invention solves the complicated problem of treating patients for Depression Disorders or Bipolar Disorders through an unusual compound profile. It is a highly selective $5HT_{2A}$ receptor antagonist having subnanomolar affinity for the $5HT_{2A}$ receptor versus affinities of greater than 100 nM for the $5HT_{2c}$, $D_1$ (dopamine), $D_2$ (dopamine), and α-1 receptors in in vitro models.

It has a lower affinity for receptors often associated with unwanted side effects, e.g., lower affinity for the $D_2$ receptor suggests less potential to cause extrapyramidal side effects, little affinity for the cholinergic M1/M2 receptors suggests less cholinergic side effects such as dry mouth, delirium and cognitive impairment. It is orally active, non-toxic at therapeutic doses and potent. It is also capable of being scaled-up for commercial synthesis. Additionally, neurochemical studies indicate that there is a serotonin/dopamine interaction following chronic administration of this compound as described in *Life Sciences* 56(25): 2209–2222 (1995), incorporated herein by reference. The combination of the foregoing characteristics produces a unique compound for treating patients having either Depressive Disorders or Bipolar Disorders.

SUMMARY OF THE INVENTION

In accordance with the present invention, a compound has been discovered which is useful in the treatment of Depressive Disorders and Bipolar Disorders, the (+)-isomer of α-(2,3-dimethoxyphenyl)-1-[2-(4-fluorophenyl)ethyl]-4-piperidinemethanol or the pharmaceutically acceptable salts thereof. It is described by the following formula:

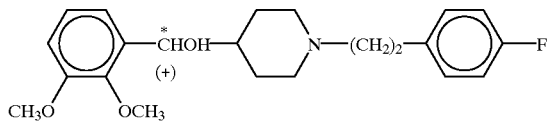

A therapeutically effective amount of this compound or its pharmaceutically acceptable acid addition salt is administered to a patient in need of such therapy to treat Depressive Disorders or Bipolar Disorders.

DETAILED DESCRIPTION OF THE INVENTION

As used in this application:

a) the expression "pharmaceutically acceptable acid addition salts" is intended to apply to any non-toxic organic or inorganic acid addition salt of the compound of the present invention. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid sales can be formed, and such salts can exist in either a hydrated or substantially anhydrous form. In general, the acid addition salts of these compounds are soluble in water and various hydrophilic organic solvents and which in comparison to their free base forms, generally demonstrate higher melting points.

b) any reference to (+)-α-(2,3-dimethoxyphenyl)-1-[2-(4-fluorophenyl)ethyl]-4-piperidinemethanol should be construed as encompassing the free base of this compound or an acid addition salt of this compound.

c) the term "patient" refers to a warm-blooded animal, such as for example rats, mice, dogs, cats, guinea pigs, and primates such as humans, and;

d) the term "treat" refers to either relieving or alleviating the patient's disease or condition.

The (+)-isomer of α-(2,3-dimethoxyphenyl)-1-(2-(4-fluorophenyl)ethyl]-4-piperidinemethanol can be prepared by methods known in the art as was discussed in European Application 0 208 235 (U.S. Pat. No. 5,169,096). One suitable method is disclosed below in Reaction Scheme I:

REACTION SCHEME I

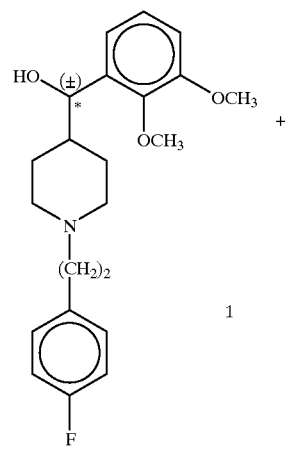

1

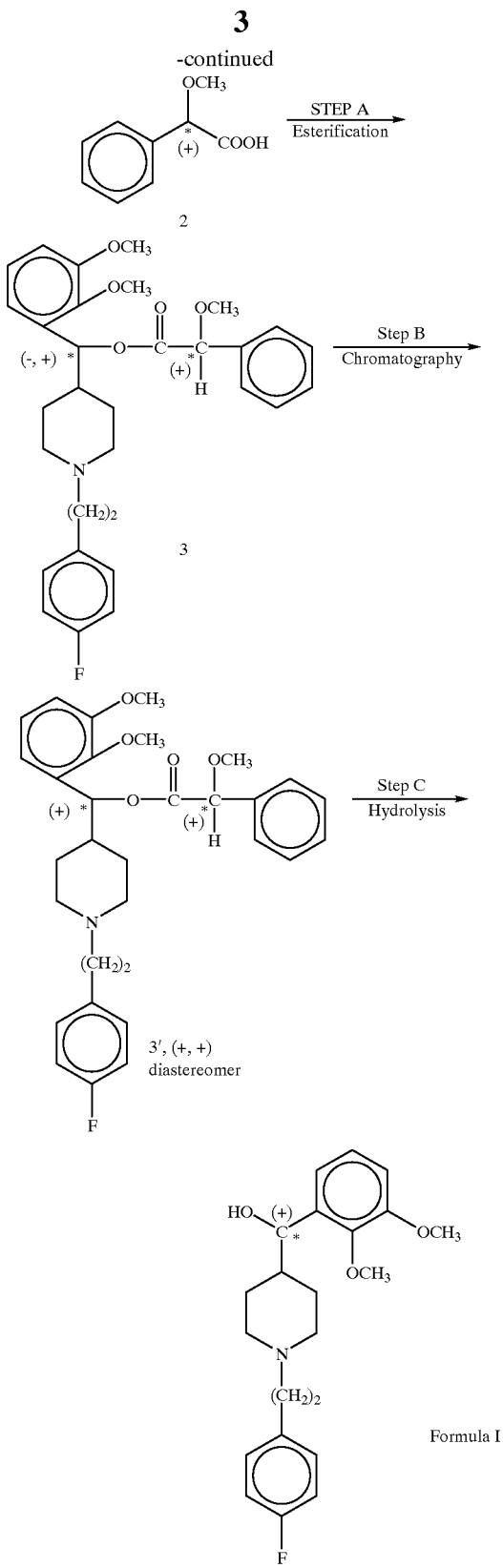

In Step A of Reaction Scheme I, an esterification reaction is carried out between racemic α-(2,3-dimethoxyphenyl)-1-[2-(4-fluorophenyl)ethyl]-4-piperidinemethanol (structure 1) and the (+)-isomer of α-methoxyphenylacetic acid (structure 2). This esterification produces the diastereomeric mixture identified as structure 3. These diastereomers are subjected to silica gel chromatography which separates the two diastereomers, thereby isolating the (+,+) diastereomer as is depicted in Step B. In Step C, the (+,+) diastereomer is hydrolysed which produces the (+)-isomer of α-(2,3-dimethoxyphenyl)-1-[2-(4-fluorophenyl)ethyl]-4-piperidinemethanol.

The esterification reaction can be carried out using techniques known in the art. Typically approximately equivalent amounts of racemic α-(2,3-dimethoxyphenyl)-1-[2-(4-fluorophenyl)ethyl]-4-piperidinemethanol and the (+)-isomer of α-methoxyphenylacetic acid are contacted in an organic solvent such as methylene chloride, THF, chloroform, toluene and heated to reflux for a period of time ranging from 5 to 24 hours. The esterification is typically carried out in the presence of an equivalent amount of dicyclohexylcarbodiimide and a catalytic amount of 4-dimethylaminopyridine. The resulting diastereomers can be isolated by filtration of the dicyclohexylurea and evaporation of the filtrate.

The diastereomers are then subjected to silica gel chromatograpy which separates the (+,+) and the (−,+) diastereomers. This chromatagraphic separation may be carried out as is known in the art. A 1:1 mixture of hexane and ethyl acetate is one suitable eluent.

The resulting (+,+) diastereomer is then subjected to a hydrolysis reaction which produces the (+)-isomer of α-(2,3-dimethoxyphenyl)-1-[2-(4-fluorophenyl)ethyl]-4-piperidinemethanol. The hydrolysis is carried out by contacting the diastereomer with an excess of a base such as potassium carbonate in an aqueous alcoholic solution. The hydrolysis is carried out at a temperature of about 15 to 30° C. for a period of time ranging from 2 to 24 hours. The resulting (+)-isomer of α-(2,3-dimethoxyphenyl)-1-[2-(4-fluorophenyl)ethyl]-4-piperidinemethanol may then be recovered by dilution with water and extraction with methylene chloride. It is then purified by recrystallization from a solvent system such as cyclohexane/hexane or ethyl acetate/hexane.

Methods for producing the starting materials of Reaction Scheme I are known in the art. For example, U.S. Pat. No. 4,783,471 teaches how to prepare racemic α-(2,3-dimethoxyphenyl)-1-[2-(4-fluorophenyl)ethyl]-4-piperidinemethanol. This patent is hereby incorporated by reference. Examples No. 1 and 2 of this application also teach suitable methods. Alternatively, racemic α-(2,3-dimethoxyphenyl)-1-[2-(4-fluorophenyl)ethyl]-4-piperidinemethanol can be prepared in the following manner. Initially In-hydroxypiperidine is subjected to an N-alkylation reaction with p-fluorophenylethyl bromide which produces 4-hydroxy-1-[2-(4-fluorophenyl)ethyl]-piperidine. This compound is brominated with $Ph_3P.Br_2$ which produces 4-bromo-1-[2-(4-fluorophenyl)ethyl] piperidine. This compound is contacted with Mg thereby forming a Grignard Reagent which is then reacted with 2,3-dimethoxybenzaldehyde which produces the desired product (±)-α-(2,3-dimethoxyphenyl)-1-[2-(4-fluorophenyl)ethyl]-4-piperidinemethanol. The (+)-isomer of α-methoxyphenylacetic acid is known in the art.

The dosage range at which (+)-α-(2,3-dimethoxyphenyl)-1-[2-(4-fluorophenyl)ethyl]-4-piperidinemethanol exhibits its ability to treat Depressive Disorders (anti-depressive disorder amount) or Bipolar Disorders (anti-bipolar disorder amount) can vary depending upon the particular disease or condition being treated and its severity, the patient, other underlying disease states the patient is suffering from, and other medications that may be concurrently administered to the patient. Generally though, this compound will exhibit its anti-Depressive Disorder or anti-Bipolar Disorder properties at a dosage range of from about 0.001 mg/kg of patient body weight/day to about 100.0 mg/kg of patient body weight/day. Preferably five (5) to twenty (20) mg. per dose is administered twice daily. The compound is typically administered from 1–4 times daily. Alternatively, it can be administered by continuous infusion. The compounds can be administered orally or parenterally to achieve these effects.

The compound of the present invention can be formulated into pharmaceutical dosage forms using techniques well known in the art. For oral administration, the compound can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compound can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compound or its salts may be dissolved in a physiologically acceptable pharmaceutical carrier and administered as either a solution or a suspension. illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compound of the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The compound may be admixed with any inert carrier and utilized in laboratory assays in order to determine the concentration of the compounds within the urine, serum, etc. of the patient as is known in the art.

The following Examples are being presented to further illustrate the invention. However, they should not be construed as limiting the invention in any manner.

EXAMPLE 1

A) 1-[2-(4-Fluorophenyl)ethyl]-4-piperidinecarboxamide

A solution of isonipecotamide (10.9 g, 85.0 mmol), 2-(4-fluorophenyl)ethyl bromide (15.7 g, 77.3 mmol), and $K_2CO_3$ (2.3 g, 167 mmol) was prepared in DMF (280 mL) and stirred under argon at 90–95° C. overnight. The cooled solution was concentrated to a white oily solid. The solid was partitioned between water and $CH_2Cl_2$. The layers were separated and the aqueous layer was extracted with $CH_2Cl_2$. The combined organic layers were washed 2× with water, dried ($MgSO_4$), filtered, and evaporated to a oily solid. The solid was recrystallized from EtOAc to afford 1-[2-(4-fluorophenyl)ethyl]-4-piperidinecarboxamide as a white powder, m.p. 177–178° C. (decomp.). Anal. Calcd for $C_{14}H_{19}FN_2O$: C, 67.18; H, 7.65; N, 11.19. Found: C, 67.25; H, 7.67; N, 11.13.

B) 4-Cyano-1-[2-(4-fluorophenyl)ethyl]piperidine

To stirred phosphorus oxychloride (25 mL, 41.12 g, 268 mmol) and sodium chloride (5.1 g, 87.3 mmol) was added 1-L[2-(4-fluorophenyl)ethyl]-4-piperidinecarboxamide (8.9 g, 35.6 mmol) portionwise. After complete addition, the solution was refluxed for 2 hours. The cooled solution was poured into dilute $NH_4OH$ to destroy the $POCl_3$. The aqueous solution was cooled to 0° C., then extracted 2× with $CH_2Cl_2$. The combined organic layers were dried ($MgSO_4$), filtered, and evaporated to afford 8.1 g of an oily solid. The solid as distilled, (b.p. 150° C., 0.1 mm Hg), to afford a clear, colorless oil that solidified. This material was crystallized from hexane to afford 4-cyano-1-[2-(4-fluorophenyl)ethyl] piperidine as white needles, m.p. 47–48° C. Anal. Calcd for $C_{14}H_{17}FN_2$: C, 72.39; H, 7.38; N, 12.06. Found: C, 72.62; H, 7.49; N, 12.12.

C) 1-[2-(4-Fluorophenyl)ethyl]-4-piperidinecarboxaldehyde

To a stirred solution of 4-cyano-1-[2-(4-fluorophenyl)-ethyl]piperidine (1.00 g, 4.3 mmol) in THF (20 mL) under argon at 0° C. was added DIBAL-H (4.6 mL of a 1.0 M solution in THF, 4.6 mmol) via syringe. After stirring overnight at room temperature, 10% aqueous HCl (25 mL) was added and the solution was stirred for 3 hours. The entire mixture was then poured into 10% aqueous NaOH (50 mL), then extractd 2× with ether. The combined organic layers were washed with brine, dried ($MgSO_4$), filtered, and evaporated to afford a pale yellow oil. The oil was chromatographed on silica gel, eluting with EtOAc. The appropriate fractions were combined and evaporated to afford an oil. This oil was distilled (b.p. 166° C., 0.05 mm Hg) to afford 1-[2-(4-fluorophenyl)ethyl]-4-piperidinecarboxaldehyde, obtained as a colorless oil. Anal. Calcd for $C_{14}H_{18}FNO$: C, 71.46; H, 7.71; N, 5.95. Found: C, 71.08, H, 7.81; N, 5.86.

D) (±)-α-(2,3-Dimethoxyphenyl)-1-[2-(4-fluorophenyl)-ethyl]-4-piperidinemethanol To a stirred solution of veratrole (0.93 g, 6.7 mmol) in THF (20 mL) under argon at 0° C. was added n-BuLi (2.7 mL of a 2.5 M solution in hexane, 6.75 mmol). After stirring 2.5 h, the solution was cooled to −78° C. and treated with 1-[2-(4-fluorophenyl)ethyl]-4-piperidinecarboxaldehyde (1.30 g, 5.5 mmol) in THF (25 mL) via an addition funnel. The cooling bath was removed and the solution was allowed to stir for 2 hours. Water was added, the layers separated, and the aqueous layer was extracted with EtOAc. The combined organic layers were washed with brine, dried ($MgSO_4$), filtered, and chromatographed on silica gel, eluting with acetone. The appropriate fractions were combined and evaporated to afford a white solid. The solid was recrystallized from hexane to afford racemic α-(2,3-dimethoxyphenyl)-1-[2-(4-fluorophenyl)ethyl]-4-piperidinemethanol as shiny white needles, m.p. 126–127° C. Anal. Calcd for $C_{22}H_{28}FNO_3$: C, 70.75; H, 7.56; N, 3.75. Found: C, 70.87; H, 7.65; N, 3.68.

EXAMPLE 2

Example 2, Steps A–F, demonstrate an alternative manner of preparing (±)-α-(2,3-dimethoxyphenyl)-1-[2-(4-fluorophenyl)-ethyl]-4-piperidinemethanol, structure 1.

A) 1-(1,1-Dimethylethyl)-1,4-piperidinedicarboxylic acid

To isonipecotic acid (107.5 g, 832 mmol) stirred in 1N NaOH (40 g NaOH in 900 mL $H_2O$) and tert-butanol (1800 mL) was added di-tert-butyl dicarbonate (200 g, 916 mmol) in portions. After stirring overnight, the solution was concentrated and the resulting water layer was acidified with aqueous HCl. This acidic aqueous layer was extracted 3× with ether. The combined organic layers were washed with water, brine, dried ($MgSO_4$), filtered, and evaporated to a white solid, which was recrystallized from EtOAc/hexane (300 mL/200 mL) to afford 1-(1, 1-dimethyl-ethyl)-1,4-piperidinedicarboxylic acid as white needles, m.p. 147–149° C.

B) 4-(N-Methoxy-N-methylcarboxamido)-1-piperidinecarboxylic acid 1,1-dimethylethyl ester To a stirred solution of 1-(1,1-dimethylethyl)-1,4-piperidinedicarboxylic acid (50.0 g, 218 mmol) in anhydrous $H_2Cl_2$ (500 mL) under $N_2$ in a 2L flask was added 1,1'-carbonyldiimidazole (38.9 g, 240 mmol) portionwise. After stirring for 1 hour, N,O-dimethylhydroxylamine hydrochloride (23.4 g, 240 mmol) was added in one portion. After stirring overnight, the solution was washed twice with 1N HCl, twice with saturated NaHCO3, once with brine, dried ($MgSO_4$), filtered, and evaporated to an oil. Distillation afforded 4-(N-methoxy-N-methylcarboxamido)-1-piperidinecarboxylic acid 1,1-dimethylethyl ester as a clear oil, b.p. 120–140° C., 0.8 mm.

C) 4-(2,3-Dimethoxybenzoyl)-1-piperidinecarboxylic acid 1,1-dimethylethyl ester n-Butyl lithium (14.5 mL of a 2.5 M solution in hexane, 36.3 mmol) was added via syringe to a stirred solution of veratrole (5.00 g, 36.2 mmol) in THF (50 mL, anhydrous) under argon at 0° C. The ice bath was removed and the mixture was allowed to stir for 90 minutes. The mixture was cooled to −78° C. and treated with 4-(N-methoxy-N-methylcarboxamido)-1-piperidinecarboxylic acid 1,1-dimethylethyl ester (9.20 g, 33.8 mmol) in THF (50 mL, anhydrous) via syringe. The cooling dry ice-acetone bath was removed and the mixture was allowed to come to room temperature. After stirring for 3 hours, saturated aqueous $NH_4Cl$ was added and the mixture was allowed to stir overnight. The layers were separated and the aqueous layer was extracted with ether. The combined organic layers were washed with brine, dried ($MgSO_4$), filtered, and evaporated to afford an amber oil. The oil was chromatographed on silica gel, eluting with 20% EtOAc in hexane. The appropriate fractions were combined and evaporated to an amber oil. The oil was distilled to afford 4-(2,3-dimethoxybenzoyl)-1-piperidinecarboxylic acid 1,1-dimethylethyl ester as a colorless oil.(b.p. 225–250° C., 0.05 mm). Anal. Calcd for $C_{19}H_{27}NO_5$: C, 65.31; H, 7.79; N, 4.01. Found: C, 65.04; H, 7.92; N, 4.11.

D) 4-(2,3-Dimethoxyphenyl)-4-piperidinylmethanone 4-(2,3-Dimethoxybenzoyl)-1-piperidinecarboxylic acid 1,1-dimethylethyl ester (7.75 g, 22.2 mmol) was dissolved in trifluoroacetic acid (50 mL, 650 mmol) and stirred for 45 minutes. The entire solution was poured into ether (900 mL) and allowed to stand overnight. Filtration yielded 4-(2,3-dimethoxyphenyl)-4-piperidinylmethanone trifluoroacetate as fine white needles, m.p. 123° C. Anal. Calcd for $C_{14}H_{19}NO_3:CF_3CO_2H$: C, 52.89; H, 5.55; N, 3.86. Found: C, 52.77; H, 5.62; N, 3.82.

The resulting 4-(2,3-dimethoxyphenyl)-4-piperidinylmethanone trifluoroacetate was dissolved in water, treated with NaOH (10% aqueous) until basic, and extracted three times with dichloromethane. The combined organic layers were washed with brine, dried ($MgSO_4$), filtered, and evaporated to afford 4-(2,3-dimethoxyphenyl)-4-piperidinylmethanone as an oil.

E) (2,3-Dimethoxyphenyl) [1-[2-(4-fluorophenyl)ethyl]-4-piperidinyl]methanone monohydrochloride A solution of 4-(2,3-dimethoxyphenyl)-4-piperidinylmethanone (8.00 g, 32.1 mmol) and 2-(4-fluorophenyl)ethyl bromide (6.52 g, 32.1 mmol) was prepared in DMF (90 mL), treated with $K_2CO_3$ (7.0 g, 50.7 mmol), then stirred and heated at 80° C. under argon overnight. The cooled solution was poured into a partition of 2/1 EtOAc/toluene and water. The layers were separated and the aqueous layer was extracted with 2/1 EtOAc/toluene. The combined organic layers were washed 2× with water, 1× with brine, dried ($MgSO_4$), filtered, and evaporated to afford 11.0 g of an oil. The oil was chromatographed on silica gel, eluting with EtOAc. The appropriate fractions were combined, concentrated, dissolved in ethyl acetate and treated with HCl/ethyl acetate. (2,3-dimethoxyphenyl)[1-[2-(4-fluorophenyl)ethyl]-4-piperidinyl]-methanone monohydrochloride was obtained as a precipitate, m.p. 225–227° C. (decomp). Anal Calcd for $C_{22}H_{26}FNO_3 \cdot HCl$: C, 64.78; H, 6.67; N, 3.43. Found: C, 64.44; H, 6.73; N, 3.41.

F) (+)-α-(2,3-Dimethoxyphenyl)-1-[2-(4-fluorophenyl) ethyl]-4-piperidinemethanol To a stirred solution of (2,3-dimethoxyphenyl)[1-[2-(4-fluorophenyl)ethyl]-4-piperidinyl]methanone (6.0 g, 16.2 mmol) in MeOH (100 mL) at 0° C. was added $NaBH_4$ (1240 mg, 32.8 mmol) in two portions, over a one hour period. After stirring overnight, the solution was concentrated to a solid. The solid was partitioned between water and ether. The layers were separated and the aqueous layer was extracted with ether. The combined organic layers were washed with brine, dried ($MgSO_4$), filtered, and evaporated to a solid. The solid was chromatographed on silica gel, eluting with acetone. The appropriate fractions were combined and evaporated to afford a white solid. The solid was recrystallized from cyclohexane to afford (±)-α-(2,3-dimethoxyphenyl)-1-[2-(4-fluorophenyl)-ethyl]-4-piperidinemethanol as white needles, m.p. 126–127° C. Anal.

Calcd for $C_{22}H_{28}FNO_3$: C, 70.75; H, 7.56; N, 3.75. Found: C, 70.86; H, 7.72; N, 3.93.

EXAMPLE 3

This example demonstrates the preparation of the compound of the present invention.

Preparation of (+)-α-(2,3-Dimethoxyphenyl)-1-[2-(4-fluorophenyl)ethyl]-4-piperidinemethanol
A) Preparation of diastereomers.

A solution of 3.90 g (10.4 mmol) of (±)-α-(2,3-dimethoxyphenyl)-1-[2-(4-fluorophenyl)ethyl]-4-piperidine-methanol, 1.74 g (10.4 mmol) of S-(+)-α-methoxyphenylacetic acid, 2.15 g (10.4 mmol) of 1,3-dicyclohexylcarbodiimide and 0.1 g of 4-dimethylaminopyridine in chloroform (75 ml) was refluxed for 17 hours, allowed to cool to room temperature and filtered. The filtrate was concentrated and chromatographed on a silica gel column eluting with ethyl acetate/hexane (1:1) to afford two diastereomers, Rf=0.1 and 0.2 (TLC EtOAc/hexane, 1:1). Intermediate fractions were rechromatographed to give additional material. Those fractions with Rf=0.2 were combined to give a single diastereomeric ester, (+,+)-(2,3-dimethoxyphenyl)[1-[2-(4-fluorophenyl)ethyl]-4-piperidinyl]methyl-α-methoxybenzeneacetate.

B) Preparation of (+)-α-(2,3-Dimethoxyphenyl)-1-[2-(4-fluoroohenyl)ethyl]-4-pieridinemethanol To a stirred solution of 0.97 g (1.9 mmol) of the above mentioned diastereomeric ester, Rf=0.2, in 25 ml of methanol was added 0.5 g (3.6 mmol) of potassium carbonate and 5.0 ml of water. After stirring 17 hours at room temperature the reaction mixture was diluted with water and extracted twice with methylene chloride. The combined extracts were washed with water, brine and dried over $MgSO_4$. After filtering, the filtrate was concentrated to an oil and crystallized from 40 ml of cyclohexane/hexane (1:1) to give (+)-α-(2,3-dimethoxyphenyl)-1-[2-(4-fluorophenyl)ethyl]-4-30 piperidinemethanol, m.p.112–113° C., $[\alpha]_D^{20}$=+13.9°.

The compound of the present invention is useful in treating patients with Depressive Disorders and Bipolar Disorders. In the Diagnostic and Statistical Manual of Mental Disorders (Third Edition-Revised) ("DSM-III-R"), incorporated herein by reference, Depressive Disorders are defined as Major Depression, Dysthymia and Depressive Disorder NOS. We also include in this category Major Depressive Episode including Chronic Type, Melancholia, and Seasonal Pattern. Bipolar Disorders include Bipolar Disorder, Cyclothymia and Bipolar Disorder NOS.

A feature of Depressive Disorders is one or more periods of depression without a history of either Manic or Hypomanic episodes. A feature of Bipolar Disorders is the presence of one or more Manic or Hypomanic Episodes usually accompanied by one or more Major Depressive Episodes. A Manic or Hypomanic Episode is a distinct period during which the predominant mood is either elevated, expansive or irritable and there are associated symptoms of the Manic Syndrome as defined in DSM-III-R. The disturbance is severe enough to cause marked impairment in occupational or social functioning.

Major Depression has one or more Major Depressive Episodes. A Major Depressive Episode is characterized by: (1) at east five of the following) depressed mood, loss of Interest in pleasure (anhedonia), significant weight loss or weight gain when not dieting, insomnia or hypersomnia, psychomotor agitation or retardation, fatigue or loss of energy, feelings of worthlessness or excessive or inappropriate guilt, diminished ability to think or concentrate, or recurrent thoughts of death including suicide; (2) it cannot be established that an organic factor initiated and maintained the disturbance; (3) there are no delusions or hallucinations for as long as two weeks in the absence of prominent mood symptoms; and (4) it is not superimposed on Schizophrenia, Schizophreniform Disorder, Delusional Disorder, or Psychotic Disorder NOS.

Dysthymia has a history of a depressed mood more days than not for at least two years and during the first two years of the disturbance, the condition does not meet the criteria for a Major Depressive Episode. The depressed mood in children and adolescents can be exhibited as irritability. Also present is at least two of the following: poor appetite or overeating, insomnia or hypersomnia, low energy or fatigue, low self-esteem, poor concentration or difficulty making decisions or feeling of hopelessness. These symptoms are not superimposed on a chronic psychotic disorder such as Schizophrenia or Delusional Disorder. Also it cannot be determined that an organic factor initiated and maintained the disturbance.

There are many ways to show that the compound of the present invention is useful in treating Depressive Disorders and Bipolar Disorders such as in animal models. See for example, "Animal Models as simulations of depression" by Paul Willner, *TiPS* 12:131–136 (April 1991); "Animal Models of Depression: An overview" by Paul Willner, *Pharmac. Ther.* 45:425–455 (1990), both of which are incorporated herein by reference. One such model is the Chronic Mild Stress Model of Depression ("CMS").

CMS uses mild stressors, such as food and water deprivation, small temperature changes, changes of cage mates, etc. Over a period of weeks of exposure to the mild stressors, the animals gradually reduce their consumption of a highly preferred sucrose solution which persists (in untreated animals) for several weeks following the cessation of stress. This decreased sensitivity to reward (the sucrose solution) reflects anhedonia, a symptom of a Major Depressive Episode (see for example, *Behavioral Pharmacol*.5:Suppl.l, p. 86 (1994) where lithium, carbamazepine and ketoconazole were evaluated in CMS; *Psychopharmacology* 93:358–364 (1987) where a tricyclic antidepressant was evaluated in CMS; *Behavioural Pharmacology*:5:344–350 (1994) where a catechol-O-methyl transferase inhibitor was evaluated in CMS).

The following CMS study was performed using the compound of the present invention (hereafter "THE COMPOUND") in comparison to known anti-depressant compound imipramine.

Male Wistar rats were brought into the laboratory two months before the start of the experiment at which time they weighed aprroximately 300 grams. Except as described below, the animals were singly housed, with food an eater freely available, and maintained on a 12 hour light/dark cycle (lights on at 8AM) at a temperature of 22±° C.

The animals were first trained to consume a 1% sucrose solution; training consisted of eight 1 hour baseline tests in which sucrose was presented, in the home cage, following 14 hours food and water deprivation; intake was measured by weighing pre-weighed bottles containing the sucrose solution at the end of the test. Subsequently, sucrose consumption was monitored, under similar conditions, at weekly intervals throughout the whole experiment.

On the basis of their sucrose intakes in the final baseline test, the animals were divided into two matched groups. One group of animals was subjected to a chronic mild stress procedure for a period of 9 consecutive weeks.

Each week of stress regime consisted of: two periods of food or water deprivation (12 and 14 hour), two periods of 45 degree cage tilt (12 and 14 h), two periods of intermittent overnight illumination (lights on and off every 2 hours), two 14 hour periods of soled cage (200 ml water in sawdust bedding), two 14 hour periods of paired housing, two 14 hour periods of low intensity stroboscopic illumination (150 flashes/min). Stressors were applied continuously throughout the day and night, and scheduled randomly. Control animals were housed in a separate room and had no contract with the stressed animals. They were deprived of food and water for the 14 hours preceding each sucrose test, but otherwise food and water were freely available in the home cage. On the basis of their sucrose intake scores following 3 weeks of stress, both stressed and control animals were each divided further into matched subgroups (n=8), and for subsequent five weeks they received daily administrations of vehicle (1ml/kg, intraperineally (ip)) imipramine (10 mg/kg, ip) or THE COMPOUND (0.002, 0.02 and 0.2 mg/kg orally). All drug injections were in a volume of 1ml/kg body weight. Drugs were administered at 10 AM and sucrose tests were carried out 24 hours following the last drug treatment. After five weeks, the treatments were terminated and after one week of withdrawal a final sucrose test was carried out. Stress was continued throughout the period of treatment and withdrawal.

Results were analyzed by multiple analysis of variance, followed by Fisher's LSD test for post hoc comparisons of means.

Chronic mild stress caused a gradual decrease in the consumption of 1% sucrose solution, in the final baseline test, sucrose intake was approximately 13 gram in both groups. Following three weeks of stress (Week 0), intakes remained at 12.4 (±0.4) grams in controls but fell to 7.2 (±0.2) grams in stressed animals (p<0.001). Such a difference between control and stressed animals treated with vehicle, persisted at similar level for the remainder of the experiment.

Imipramine had no significant effect on the sucrose intake in control animals [F(1,84)=0.364; NS]. However, the drug caused a gradual increase of sucrose intake in stressed animals (F(1,84)=16.776; p<0.001]. Sucrose intake in imipramine-treated stressed animals was significantly increased from Week 0 scores after four weeks of treatment (p=0.05) and after five weeks of treatment there were no significant differences between drug-treated stressed animals and drug- and saline-treated controls. The increase of sucrose intake in imipramine-treated stressed animals was maintained at similar level one week after withdrawal from the drug.

THE COMPOUND had no significant effect on the sucrose intake in control animals [Treatment effect:F(3, 168)=0.821; NS Treatment x Weeks interaction: F(15,168=0.499; NS]. In stressed animals, THE COMPOUND gradually reversed the CMS-induced deficit in sucrose intake, resulting in a significant Treatment effect [F(3,168)=22.567; p<0.001] and Treatment x Weeks interaction (F(15,158)=1.559; p=0.05].

In stressed animals treated with two higher doses of THE COMPOUND (0.02 and 0.2 mg/kg), sucrose intakes were significantly increased from initial scores (Week 0) after two (0.02 mg/kg) and three (0.2 mg/kg) weeks of treatment (p=0.03 and p=0.04, respectively). This effect was increased further during next weeks, and at the end of treatment period (Week 5) the amount of sucrose solution drunk by these animals was comparable to that of vehicle-treated controls and significantly higher than that of vehicle-treated stressed animals (0.02 mg/kg: p<0.001, 0.2 mg/kg: p-0.002).

At the lowest dose of 0.002mg/kg., THE COMPOUND had no significant effect on the sucrose intake throughout the whole treatment period. In consequence, after five weeks of treatment the sucrose consumption of stressed animals treated with this dose did not differ from the intakes of the vehicle-treated stressed animals (p=0.860) and was significantly lower than the intakes of vehicle-treated controls (p<0.01). One week after withdrawal from the treatment, the sucrose intakes were not significantly changed in all of THE COMPOUND -treated control (0.002 mg/kg:p=0.2, 0.02 mg/kg: p=0.9, 0.2 mg/kg: p=0.4) and stressed animals (0.002 mg/kg: p=0.6, 0.02 mg/kg: p=0.8, 0.2 mg/kg: p=0.6).

Of course, clinical trials on humans may also be used to show the usefulness of the compound of the present invention in treating depression such as using the Abbreviated Hamilton Psychiatric Rating Scale for Depression. This comprises a series of 17 categories in which the individual is rated, e.g., for depressed mood, guilt, suicide tendancies, insomnia, anxiety, etc., to reach a score which indicates to the clinician whether or not the patient is suffering depression.

What is claimed is:

1. A method of treating a patient for Bipolar Disorder comprising administering to the patient an effective amount of (+)-α-(2,3-dimethoxyphenyl)-1-[2-(4-fluorophenyl) ethyl]-4-piperidinemethanol or its pharmaceutically acceptable acid addition salt.

* * * * *

UNITED STATES PATENT AND TRADEMARK OFFICE
CERTIFICATE OF CORRECTION

PATENT NO. : 6,022,877
DATED : February 8, 2000
INVENTOR(S) : Cesare Mondadori

It is certified that error appears in the above-indentified patent and that said Letters Patent is hereby corrected as shown below:

Column 2, Line 26 patent reads " sales" and should read -- salts --

Column 4, Line 49 patent reads "In-hydroxypiper..." and should read -- 4-hydroxypiperidine --

Column 6, Line 28 patent reads "a(n) oily" and should read -- a oily --

Column 6, Line 37 patent reads "1-L[2-(" and should read -- 1-[2-( --

Column 6, Line 44 patent reads "as distilled" and should read -- was distilled --

Column 6, Line 58 patent reads "extract(e)d" and should read -- extracted --

Column 7, Line 42 patent reads "$H_2Cl_2$" and should read -- $CH_2Cl_2$ --

Column 7, Line 47 patent reads "NaHCO3" and should read -- $NaHCO_3$ --

Column 9, Line 20 patent reads "fluoroohenyl" and should read -- fluorophenyl --

Column 9, Line 20 patent reads "pieridinemethanol" and should read -- piperidinemethonol --

UNITED STATES PATENT AND TRADEMARK OFFICE
CERTIFICATE OF CORRECTION

PATENT NO.   : 6,022,877
DATED        : February 8, 2000
INVENTOR(S)  : Cesare Mondadori It is certified that error appears in the above-indentified patent and that said Letters Patent is hereby corrected as shown below:

Column 9, Line 31 patent reads "4-30 piperidine..." and should read -- -4-piperdine... --

Column 9, Line 55 patent reads "east" and should read -- east --

Column 10, Line 41 patent reads "imipramine" and should read -- Imipramine --

Column 10, Line 44 patent reads "ap(p)roximately and should read -- approximately --

Signed and Sealed this

Tenth Day of April, 2001

Attest:

NICHOLAS P. GODICI

Attesting Officer     Acting Director of the United States Patent and Trademark Office